United States Patent [19]

Stone et al.

[11] 4,104,471

[45] Aug. 1, 1978

[54] METHOD OF ADDING AMINES TO 1,3 DIENES

[75] Inventors: Francis Gordon Albert Stone, Bristol; Michael Green, Chew Stoke; Gary Scholes; John Lionel Spencer, both of Bristol, all of England

[73] Assignee: Air Products & Chemicals, Inc., Allentown, Pa.

[21] Appl. No.: 775,822

[22] Filed: Mar. 9, 1977

[51] Int. Cl.² ............... C07D 295/02; C07D 211/14; C07C 87/24
[52] U.S. Cl. ........................... 544/178; 252/431 P; 260/293.51; 260/583 H
[58] Field of Search ............ 260/583 H, 247, 293.51; 252/431 R, 431 P

[56] References Cited

U.S. PATENT DOCUMENTS

| 3,435,058 | 3/1969 | Rinehart | 252/431 R X |
| 3,479,379 | 11/1969 | Ketley | 252/431 R X |
| 3,530,187 | 9/1970 | Shryne | 260/583 H |
| 3,891,684 | 6/1975 | Jung | 252/431 P X |

Primary Examiner—Winston A. Douglas
Assistant Examiner—John J. Doll
Attorney, Agent, or Firm—Russell L. Brewer; Barry Moyerman

[57] ABSTRACT

A method of producing 1:2 amine-diene adducts which method comprises contacting a sterically unhindered amine with a 1,3 diene in the presence of a catalytic amount of a catalyst comprising an olefin-palladium complex preferably of the type X—Pd—X where X is an olefin and Pd is palladium in its zero valent state.

1 Claim, No Drawings

METHOD OF ADDING AMINES TO 1,3 DIENES

This invention relates to the addition of amines to 1,3 dienes.

As reported in J.C.S. Perkin II, 1511 (1974) and 1133 (1975) it is known to react amines with 1,3 dienes in the presence of a nickel catalyst and phosphine co-catalyst to produce a mixture of 1,3,7 octatriene and substantial quantities of 1:1 and 1:2 amine-diene adducts.

It is also known that amines will react with 1,3 dienes in the presence of a catalyst mixture of palladium (O) complexes with two molar equivalents of phosphine co-catalyst to produce a mixture of organics including octatrienes and 1:1 and 1:2 amine-diene adducts.

It is an object of at least preferred embodiments of the present invention to provide a method of adding amines to 1,3 dienes to produce a product comprising 1:2 amine-diene adducts and little or no 1:1 amine-diene adducts.

Accordingly the present invention provides a method of producing 1:2 amine-diene adducts, which method comprises contacting a sterically unhindered amine with a 1,3 diene in the presence of a catalytic amount of a catalyst comprising an olefin-palladium complex.

The 1,3 diene may comprise, for example butadiene or isoprene.

The amine is preferably secondary and may comprise for example, alicyclic or heterocyclic amines such as morpholine, or dialkylamines such as dimethylamine or diethylamine. The amine could however be primary. Our research has indicated that no reaction occurs if the amine is sterically hindered, e.g. diisopropylamine. The amine should preferably also be non-bulky to avoid excessive reaction times.

The catalyst is preferably of the type X—Pd—X where X is an olefin and Pd is palladium in its zerovalent state.

A particularly suitable catalyst is bis(cyclo-octa-1,5-diene)palladium.

Where isomeric 1:2 amine-diene adducts are formed, their yield and distribution may be influenced by the addition of a co-catalyst such as phosphine. One particular catalyst mixture comprises an olefin-palladium complex and a phosphine co-catalyst mixed in the ratio 1 mole of phosphine co-catalyst to 1 mole of palladium complex. Advantageously such a mixture comprises bis(cyclo-octa-1,5-diene)palladium and triphenylphosphine.

The mixture is usually heated preferably to at least 50° C. and more preferably to about 60° C.

The reaction is preferably carried out at a pressure greater than atmospheric especially in the range 6-7 atmospheres.

The yield of 1:2 amine-diene adducts may, in some cases, be improved by the addition of acetic acid.

For a better understanding of the invention reference will now be made to the following examples which are given for illustrative and not restrictive purposes.

In each example reactions were performed at 60° C. in Carius tubes fitted with Young pressure taps under approximately 6-7 atmospheres of butadine. Reagent amines were dried over potassium hydroxide, and distilled prior to use. Butadiene was distilled into the reaction vessel on a vacuum line. Triphenylphosphine was recrystallised from benzene-light petroleum (B.P. 100°-120° C.). Bis(cyclo-octa-1,5-diene)palladium was prepared as described in applicants U.S. Pat. application having Ser. No. 641,407 and a filing date of Dec. 17, 1975, and introduced in catalytic amounts into the reaction vessel at temperatures below −30° C. Products were distilled from the catalyst and analysed by a gas chromatograph connected to a mass spectrometer.

EXAMPLE 1

A mixture comprising:
32mg (0.1mmol) bis(cyclo-octa-1,5-diene)palladium;
4.3g (50mmol) morpholine; and
8.1g (150mmol) 1,3 butadiene
was heated at 60° C. for 17 hours.

80% of the morpholine was converted into 1:2 amine-diene adducts 1 and II shown below in the ratio of 16.4:83.5. A small amount of 1,3,7-octatriene and 4-vinyl-cyclohexene was also isolated.

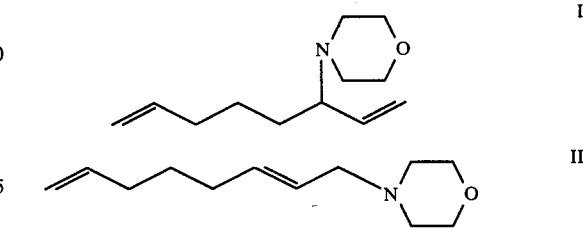

EXAMPLE 2

A mixture comprising:
32mg (0.1mmol) bis(cyclo-octa-1,5-diene)palladium;
26mg (0.1mmol) triphenylphosphine;
4.3g (50mmol) morpholine; and
8.1g (150mmol) 1,3 butadiene
was heated at 60° C for 17 hours.

100% of the morpholine was converted into 1:2 amine-diene adducts comprising 98% of isomer II shown in example 1.

EXAMPLE 3

A mixture comprising:
32mg (0.1mmol) bis(cyclo-octa-1,5-diene)palladium;
1.3g (18mmol) diethylamine; and
3.0g (54mmol) butadiene
was heated at 60° C for 17 hours.

20% of the diethylamine was converted to 1:2 amine-diene adduct III.

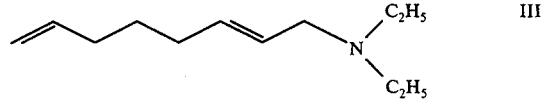

EXAMPLE 4

A mixture comprising:
32mg (0.1mmol) bis(cyclo-octa-1,5-diene)palladium;
1.3g (18mmol) diethylamine;
3.0g (54mmol) butadiene; and
26mg (0.1mmol) triphenylphosphine
was heated at 60° C. for 17 hours.

20% of the diethylamine was converted into 1:2 amine-diene adduct III.

EXAMPLE 5

A mixture comprising:
32mg (0.1mmol) bis(cyclo-octa-1,5-diene)palladium;

4.2g (50mmol) piperidine; and
8.1g (150mmol) butadiene
was heated at 60° C for 17 hours.

80% of the piperidine was converted to 1:2 amine-diene adduct IV.

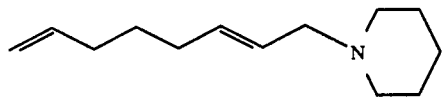

IV

EXAMPLE 6

A mixture comprising:
32mg (0.1mmol) bis(cyclo-octa-1,5-diene)palladium;
26mg (0.1mmol) triphenylphosphine;
4.2g (50mmol) piperidine; and
8.1g (150mmol) butadiene
was heated at 60° C for 17 hours.

85% of the piperidine was converted to 1:2 amine-diene adduct IV.

EXAMPLE 7

A mixture comprising:
32mg (0.1mmol) bis(cyclo-octa-1,5-diene)palladium;
2.0g (44mmol) dimethylamine; and
7.0g (132mmol) butadiene
was heated at 60° C for 17 hours.

20% of the dimethylamine was converted to 1:2 amine-diene adducts V and VI in the ratio 43:52.2

EXAMPLE 8

A mixture comprising:
32mg (0.1mmol) bis(cyclo-octa-1,5-diene)palladium;
26mg (0.1mmol) triphenylphosphine;
2.0g (44mmol) dimethylamine; and
7.0g (132mmol) 1,3 butadiene
was heated at 60° C for 17 hours.

20% of the dimethylamine was converted into 1:2 amine-diene adducts V and VI in the ratio 43:52.2

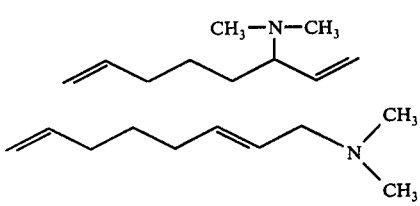

V

VI

EXAMPLE 9

A mixture comprising:
32mg (0.1mmol) bis(cyclo-octa-1,5-diene)palladium;
7.0g (97mmol) diethylamine;
6.0g (100mol) acetic acid; and
1.5g (213mmol) 1,3 butadiene
was heated at 60° C for 17 hours.

45% of the diethylamine was converted into the 1:2 amine-diene adducts III.

It will be noted that the addition of the acetic acid (which probably acted as an intermediate) increased the yield of 1:2 amine-diene adduct III from 20% (Examples 3 and 4) to 45%.

EXAMPLE 10

A mixture comprising:
32mg (0.1mmol) bis(cyclo-octa-1,5-diene)palladium;
1.5g (17.4mmol) morpholine; and
3.4g (50mmol) isoprene
was heated at 60° C for 17 hours.

85% of the morpholine was converted into amine-diene adducts VII, VIII and IX in the ratio 66.7:23.4:9.9

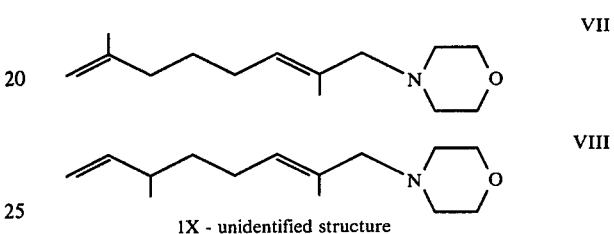

VII

VIII

IX - unidentified structure

EXAMPLE 11

A mixture comprising:
32mg (0.1mmol) bis(cyclo-octa-1,5-diene)palladium;
26mg (0.1mmol) triphenylphosphine;
1.5g (17.4mmol) morpholine; and
3.5g (51.4mmol) isoprene
was heated at 60° C for 17 hours.

51% of the morpholine was converted to 1:2 amine-diene adducts VII, VIII and IX in the ratio 74.5:17:8.5.

It will be noted that in this example the triphenylphosphine co-catalyst surpressed the conversion of 1:2 amine-diene adducts.

In each of the above examples, the presence of 1:1 amine-diene adducts was not detected in the product and hence any such adducts were either absent or present in only trace amounts.

We claim:

1. In a process for dimerizing a conjugated olefin in the presence of a secondary amine by contacting the conjugated olefin and amine with a palladium catalyst, the improvement for obtaining enhanced yields of dimers while minimizing the formation of trimers and producing 1:2 amine-diene adducts with little to no 1:1 amine diene adducts which comprises: reacting a conjugated olefin selected from the group consisting of butadiene and isoprene with a secondary amine selected from the group consisting of morpholine, piperidine, dimethylamine, and diethylamine in the presence of a complex of bis(cyclo-octa-1,5-diene)palladium and a tertiary phosphine ligand in a 1:1 mole ratio as the palladium catalyst at a temperature of from 50°-60° C and a pressure of from 6-7 atmospheres.

* * * * *